(12) United States Patent
Fourneaud et al.

(10) Patent No.: US 8,994,386 B2
(45) Date of Patent: Mar. 31, 2015

(54) METHOD AND DEVICE FOR MEASURING PERMITTIVITY AND/OR PERMEABILITY

(75) Inventors: Ludovic Fourneaud, Grenoble (FR); Laurent Dussopt, Grenoble (FR)

(73) Assignee: Commissariat à l'énergie atomique et aux énergies alternatives, Paris (FR)

( * ) Notice: Subject to any disclaimer, the term of this patent is extended or adjusted under 35 U.S.C. 154(b) by 808 days.

(21) Appl. No.: 13/256,294

(22) PCT Filed: Mar. 2, 2010

(86) PCT No.: PCT/EP2010/052605
§ 371 (c)(1),
(2), (4) Date: Dec. 2, 2011

(87) PCT Pub. No.: WO2010/102925
PCT Pub. Date: Sep. 16, 2010

(65) Prior Publication Data
US 2012/0098554 A1 Apr. 26, 2012

(30) Foreign Application Priority Data
Mar. 13, 2009 (FR) ...................................... 09 51598

(51) Int. Cl.
*G01R 27/26* (2006.01)
*G01N 22/00* (2006.01)

(52) U.S. Cl.
CPC ............ *G01R 27/2617* (2013.01); *G01N 22/00* (2013.01)
USPC ....................................................... 324/693

(58) Field of Classification Search
CPC .................................................. G01R 27/2617
USPC ......................................................... 324/693
See application file for complete search history.

(56) References Cited

U.S. PATENT DOCUMENTS 3,628,135 A * 12/1971 Reed .............................. 324/640
4,991,128 A * 2/1991 Evans et al. ...................... 702/77

(Continued)

FOREIGN PATENT DOCUMENTS

FR 2619223 2/1989
FR 2651580 3/1991

(Continued)

OTHER PUBLICATIONS

Huynen et al "A Wideband Line-Line Dielectrometic Method for Liquids, Soils and Planar Substates" IEEE Transactions on Instrumentation and Measurement, 50:5, 2001.

(Continued)

*Primary Examiner* — Jeff Natalini
(74) *Attorney, Agent, or Firm* — Occhiuti & Rohlicek LLP (57) ABSTRACT

The invention relates to a method for measuring the permittivity and/or perviousness of a sample of a nonconductive material, said method comprising: a) measuring a value representative of an admittance $Y_{testco}$, b) measuring a value representative of an admittance $Y_{testcc}$ only from the amplitude and the phase of the electromagnetic waves reflected onto an interface between the sample and the end of a second waveguide having at least one conductive web separated from a conductive sheath by a layer of dielectric material, said second waveguide also including a short circuit between the central web and the sheath at the interface with the sample, and c) calculating the permittivity of the sample from the values representative of the admittances $Y_{testco}$ and $Y_{testcc}$ and/or calculating the perviousness of the sample from the values representative of the admittances $Y_{testco}$ and $Y_{testcc}$.

9 Claims, 3 Drawing Sheets

(56) References Cited

U.S. PATENT DOCUMENTS

| | | |
|---|---|---|
| 5,132,623 A | 7/1992 | De et al. |
| 6,617,851 B1 * | 9/2003 | Bergmann .................... 324/318 |
| 7,239,687 B1 * | 7/2007 | Olofsson et al. ........... 379/29.01 |
| 2004/0246069 A1 * | 12/2004 | Yoneda et al. ................ 333/125 |
| 2007/0090846 A1 | 4/2007 | Habashy et al. |
| 2008/0191711 A1 | 8/2008 | Rivera |

FOREIGN PATENT DOCUMENTS

| | | |
|---|---|---|
| FR | 2698168 | 5/1994 |
| FR | 2792417 | 10/2000 |
| JP | 2002214161 | 7/2002 |

OTHER PUBLICATIONS

Moukanda et al. "A Cavity in Transmission for Extracting Electric Parameters of Thin Layers" Signals, Systems and Electronics 431-434, 2007.

Ng et al. "An Automated Microwave Waveguide Measurement Technique" Microwave Conference 1322-1325, 2008.

\* cited by examiner

METHOD AND DEVICE FOR MEASURING PERMITTIVITY AND/OR PERMEABILITY

CROSS REFERENCE TO RELATED APPLICATIONS

This application is the national stage entry under 35 USC 371 for: PCT/EP2010/052605, filed on Mar. 2, 2010, which claims the benefit of the Mar. 13, 2009 priority date of French application 0951598. The contents of both the foregoing application are incorporated herein by reference.

The invention pertains to a method and device for measuring the permittivity and/or the permeability of a sample of non-conductive material.

Herein, barring indications to the contrary, the term "permittivity" designates relative dielectric permittivity and the term "permeability" designates relative magnetic permeability.

There are methods for measuring the permittivity of samples of non-conductive material comprising steps of:

a) measuring a variable representing an admittance $Y_{testco}$ solely from the amplitude and phase of electromagnetic waves reflected on an interface between the sample and one end of a first waveguide, this end having at least one core separated from a conductive sheath by a layer made of dielectric material in which the electromagnetic waves are propagated.

For example, a method of this kind is disclosed in the French patent FR 2 651 580.

Herein, a sample of material is considered to be non-conductive if its conductivity is below $10^{-2}$ S·m$^{-1}$ and preferably below $10^{-3}$ S·m$^{-1}$.

These prior-art methods are also known as methods of "electromagnetic characterization in reflection" because they only use the reflection of the magnetic waves on the sample to measure the permittivity.

These methods of measurement by reflection have many advantages. For example, they make it possible to:

carry out measurements on liquid, solid or soft materials (powders, elastic materials etc), carry out non-destructive measurements because it is not necessary to machine the solid sample to give it a specific shape other than a plane shape, and characterize the material on a wide range of frequencies (for example 0 MHz to 20 GHz).

However, prior-art methods have the drawback of not being capable of implementation on samples having permeability different from 1. Thus, with these prior-art methods, it is not possible, for example to measure the permittivity of a ferrite.

Furthermore, it is only permittivity that can be measured with these prior-art methods, and not magnetic permeability.

To overcome these drawbacks, methods for measuring permittivity and permeability have been developed. These methods use, in addition to reflection, the transmission of electromagnetic waves through the sample. A method of measurement by reflection and transmission of this kind is described in the patent application US 2007 09 08 46.

These methods of measurement by reflection and transmission necessitate the machining or conformation of the sample to enable it to be housed within an electromagnetic waveguide. This is a drawback.

To overcome this drawback, the US patent application 2008/191711 proposes to use two waveguides placed one beside the other on the same side of the sample. Electromagnetic waves are sent out in the first waveguide. A part of these waves is reflected on the sample at the interface with the sample and another part gets propagated through the sample up to the second waveguide. Then, the permittivity or the permeability is measured from the reflected and transmitted electromagnetic waves. However, the fact that a part of the measurements are made in transmission imposes major constraints. For example, the distance between the two waveguides must be known with precision. Furthermore, this approach always dictates the simultaneous use of two waveguides.

The invention is aimed at overcoming at least one of these drawbacks.

An object of the invention therefore is a method for measuring the permittivity and/or permeability of a sample of non-conductive material comprising:

b) the measurement of a magnitude or variable representing an admittance $Y_{testcc}$ solely from the amplitude and the phase of the electromagnetic waves reflected on the interface between the sample and the end of a second waveguide having at least one conductive core separated from a conductive sheath by a layer of dielectric material in which the electromagnetic waves get propagated, the second waveguide also comprising a short-circuit between the central core and the sheath made at the interface with the sample so that the phase and/or the amplitude of the electromagnetic waves reflected on the sample are different from those obtained when there is no short-circuit, and c) the computing of the permittivity of the sample from the variables representing values of admittance $Y_{testco}$ and $Y_{testcc}$ and/or computing the permeability of the sample from the variables representing the values of admittance $Y_{testco}$ and $Y_{testcc}$.

The above method can be used to measure the permittivity of samples having a permeability equal to 1 as well as of samples having a permeability different from 1. For example, the permeability of ferrite can be measured by means of the above method.

The above method also enables the measurement, purely by reflection of electromagnetic waves on the sample, of both the permeability and the permittivity of this sample.

These results are achieved without using any measurement in transmission. More specifically, the use of a short-circuit, here below called a "partial" short-circuit, to modify the phase and/or amplitude of the waves reflected by the sample advantageously replaces the commonly used method of making measurements in transmission. The problems related to the performance of measurement by transmission are therefore averted. Such a partial short-circuit can be distinguished from the known short-circuits used during the calibration phase. Known short-circuits are used to measure the characteristics of the waveguides. These known short-circuits are not implemented to measure characteristics of the sample. On the contrary, these known short-circuits are used to isolate the waveguide from the sample so that they are sensitive only to the characteristics of the waveguide.

Finally, the above method also preserves all the advantages related to measurement solely by reflection as compared with the methods of measurement by reflection and transmission.

The embodiments of this method may comprise one or more of the following characteristics:

between the steps a) and b), the method comprises the switching over of a switch electrically connected between the core and the sheath to pass from the first waveguide where the core and the sheath are electrically insulated from each other to the second waveguide where the core and the sheath are electrically short-circuited;

the measurements of the variables representing admittance values $Y_{testco}$ and $Y_{testcc}$ are made with electromagnetic waves of a same frequency.

These embodiments of the method furthermore have the following advantage:

the switching over of a switch to make it pass from the first waveguide to the second waveguide enables a speedy change from the measurement of the admittance $Y_{testco}$ to the measurement of the admittance $Y_{testcc}$ and vice-versa.

An object of the invention is also an information-recording medium comprising instructions for the implementing of the above method when the instructions are executed by an electronic computer.

An object of the invention is also a device for measuring the permittivity and/or permeability of a sample of non-conductive material, this device comprising:

an apparatus for measuring admittance values solely from the amplitude and the phase of the electromagnetic waves reflected on an interface between the sample and an end of a guide of these electromagnetic waves, a first waveguide having a first end capable of being applied to the sample and a second opposite end capable of being connected to the measuring apparatus to measure a variable representing an admittance $Y_{testco}$, this first waveguide being equipped with at least one core separated from a conductive sheath by a layer made of dielectric material in which the electromagnetic waves are propagated a second waveguide having a first end capable of being applied to the sample and a second opposite end capable of being connected to the measuring apparatus to measure a variable representing an admittance $Y_{testcc}$, this second waveguide being equipped with at least one conductive core separated from a conductive sheath by a layer of dielectric material in which the electromagnetic waves get propagated, the second waveguide also comprising a short-circuit between the central core and the sheath made at the interface with the sample so that the phase and/or the amplitude of the electromagnetic waves reflected on the sample are different from those obtained when there is no short-circuit, and a computer capable of computing the permittivity of the sample from the variables representing values of admittance $Y_{testco}$ and $Y_{testcc}$ and/or computing the permeability of the sample from the variables representing the values of admittance $Y_{testco}$ and $Y_{testcc}$.

The embodiments of this device may comprise one or more of the following characteristics:

the core, the sheath and the dielectric material of the first and second waveguides are common, and the device comprises a switch electrically connected between the core and the sheath to pass from the first waveguide where the core and the sheath are electrically insulated from one another to the second waveguide where the core and the sheath are short-circuited;

the first end of the second waveguide comprises a metal plate extending from the central core to the sheath to short-circuit the core and the sheath and obstruct only one part of the section of the dielectric material in which the electromagnetic waves reflected on the sample get propagated;

the second waveguide is identical to the first waveguide except that it comprises said metal plate;

the sheath entirely surrounds the core.

These embodiments furthermore have the following advantage:

having first and second waveguides that are almost identical makes it possible to have working frequency ranges for these guides that are also almost identical.

The invention will be understood more clearly from the following description given purely by way of a non-restrictive example and made with reference to the drawings of which.

In these figures, the same references are used to designate the same elements.

Here below in this description, the characteristics and functions well-known to those skilled in the art are not described in detail.

Figure 1:
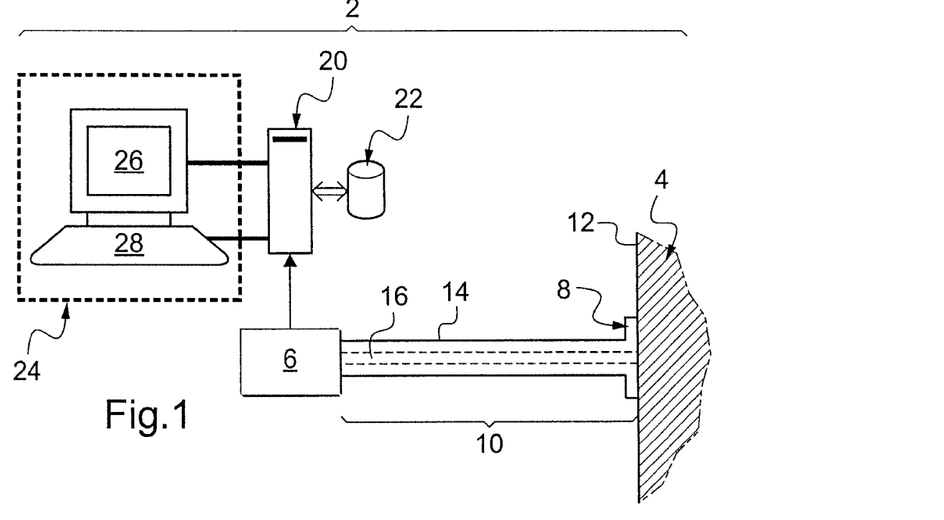
FIG. 1 is a schematic illustration of a device for measuring the permittivity and the permeability of a sample of non-conductive material.

FIG. 1 shows a device 2 for measuring the permittivity and the permeability of a sample 4 made of non-conductive material. As an illustration, the sample 4 is a sample made out of a material whose permeability is different from 1. For example, the sample 4 is a ferrite. The sample 4 may be a part of an object or the totality of this object.

The device 2 has an apparatus 6 for measuring admittance at the interface between the sample 4 and a probe 8 forming the end of an electromagnetic waveguide 10. The admittance, denoted as Y, is the reciprocal of the impedance.

Another end of the guide 10 is electrically connected to the apparatus 6.

Here, the apparatus 6 is capable of generating electromagnetic waves which are directed by the waveguide 10 up to the plane face 12 of the sample 4. To this end, the probe 8 is directly applied to the face 12. The apparatus 6 measures the amplitude and phase of the waves reflected at the interface with the sample 4.

For example, the apparatus 6 is a vectorial network analyzer (VNA). These analyzers are known and shall not be described herein in greater detail.

By way of an illustration, the apparatus 6 is connected to an electronic computer 20 capable of computing the permittivity and the permeability of the sample 4 from values of admittance measured by the apparatus 6. For example, the computer 20 is a programmable electronic computer capable of executing instructions recorded on an information-recording medium. To this end, the computer 20 is connected to a memory 22 comprising the instructions needed to execute the method of FIG. 5.

The waveguide 10 is formed by a conductive sheath 14 which extends around a central conductive core 16. The sheath 14 and the core 16 are for example made of metal. The sheath 14 and the core 16 are separated from each other by a dielectric material in which the guided electromagnetic waves get propagated. For example, the waveguide 10 is a coaxial cable.

The computer 20 is also connected to a man-machine interface 24 to communicate the measured values of permittivity and permeability to a user. For example, the interface 24 is herein formed by a screen 26 and a keyboard 28.

Figure 2:
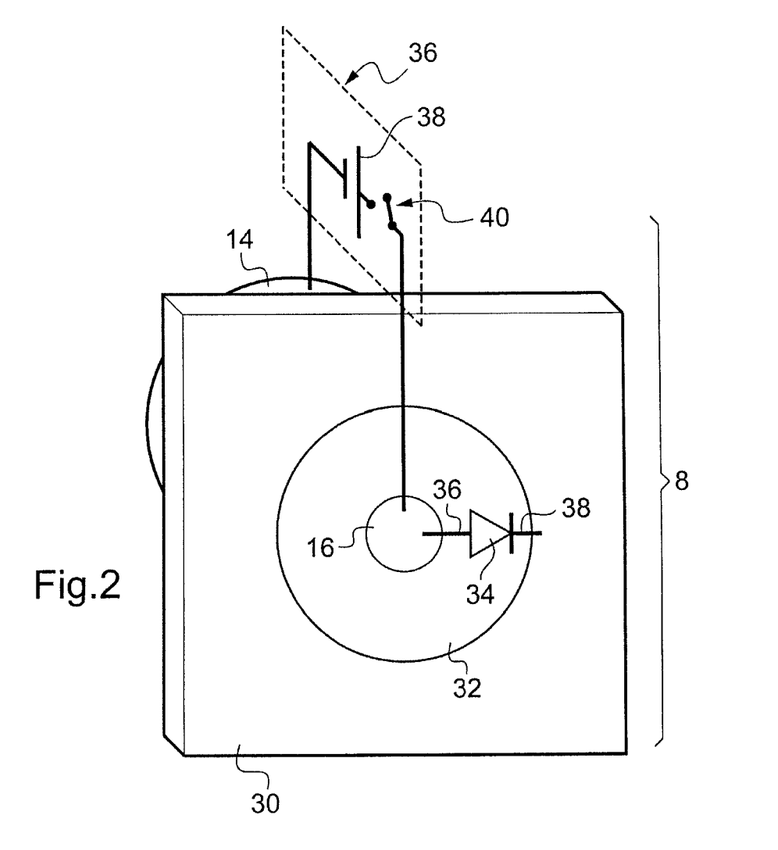
FIG. 2 is a schematic illustration in perspective of the end of a waveguide of the device of FIG. 1, FIGS. 3 and 4 are schematic illustrations of the end shown in FIG. 2 in an open-circuit configuration and in a partial short-circuit configuration as well as an illustration of the corresponding electrical models.

FIG. 2 shows the probe 8 in greater detail.

The probe 8 has a clamp 30 designed to be lean directly on the face 12 of the sample 4. This clamp 30 surrounds the sheath 14.

Between the sheath 14 and the core 16, there is housed a dielectric material 32 that electrically insulates the core 16 from the sheath 14. Here, substantially in the plane of the clamp 30, the core 16 is electrically connected to the sheath 14 by means of a controllable switch 34. In its closed position, the switch 34 short-circuits the core 16 and the sheath 14. In its open position, on the contrary, the core 16 and the sheath 14 are electrically insulated from each other. The dimensions of this switch 34 as well as those of the electrical conductors 36 and 28 that connect them, respectively, to the core 16 and the sheath 14 are chosen so that, in the closed position, a part of the electromagnetic wave gets reflected all the same on the sample 4. To this end, when the switch is closed, the short-circuit blocks only one part of the cross-section of the dielectric material 32. This short-circuit modifies the phases of the electromagnetic waves reflected on the face 12 relatively to the case where the switch 34 is in its open position. Thus, in closed position, this short-circuit is a partial short-circuit. The dimensions of the switch 34 and of the conductors 36 and 38 can also be chosen so that the closing of the switch 34 also gives rise to a modification of the amplitude of the electromagnetic waves reflected on the face 12 in relation to the case where the switch 34 is in its open position. For example, these modifications of the phase and/or of the amplitude are at least greater than 1% or 10% of the phase and/or of the amplitude obtained when the switch 34 is in its open position.

Preferably, in its closed position, the dimensions of the switch 34 and of the conductors 36 and 38 are chosen in such a way that the short-circuit created corresponds also to an electromagnetic short-circuit capable of introducing an 180° phase shift relatively to the situation where the switch 34 is in its open position.

Many different embodiments are possible for the switch 34. For example, the switch 34 can be made by means of:
  semiconductor components such as diodes, transistors or thyristors,
  mechanical microsystems (MEMS), or again:
  optoelectronic components (phototransistors).

For example, in FIG. 2, the switch 34 is made by means of a diode.

The device 2 also has a unit 36 for controlling the switch 34. This unit 36 is capable of controlling the switch-over of the switch 34 between its open and closed positions. For example, the switch-over between the open and closed positions is activated manually by a user.

In the case of a diode, the unit 36 has, for example, a DC voltage source 38 connected between the sheath 14 and the core 16. This source 38 is series-connected with a selector switch 40. When the selector switch 40 is in a closed position, a DC voltage is applied between the core 16 and the sheath 14. This DC voltage is chosen so as to turn the diode 34 on. When the selector switch 40 is in its open position, no DC voltage is applied between the sheath 14 and the core 16 so that the diode 34 is in its open position and therefore does not let current pass through.

When the switch 34 is in its closed position, it allows the AC current at the working frequency to get propagated from the core 16 up to the sheath 14 by conductivity. Conversely, when the switch 34 is in its open position, this AC current at the working frequency cannot get propagated by conductivity of the core 16 up to the sheath 14.

The selector switch 40 is switched over between its open and closed positions manually by an operator. For example, the selector switch 40 is a push-button.

Figure 3:
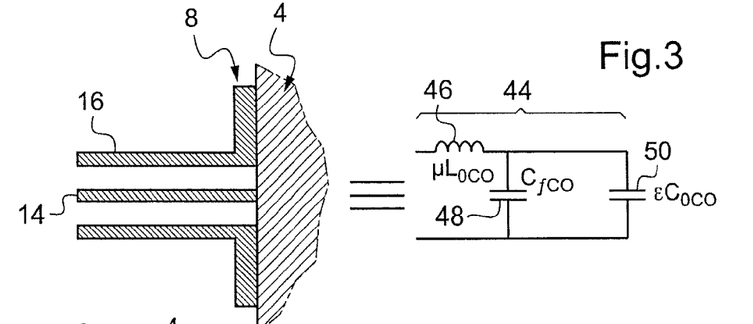

FIG. 3 is a schematic cross-section view of the probe 8 when the switch 34 is in its open position. This probe is then said to be in an open circuit. In this state, the interface between the end 8 and the sample 4 can be modeled with an electrical model 44. Here, this electrical model 44 comprises an inductor 46 series-connected with a capacitor 48. A capacitor 50 is also parallel-connected with the terminals of the capacitor 48. The value $\mu L_{0co}$ of the inductor 46 is proportional to the permeability $\mu$ of the sample 4. The capacitance $C_{fco}$ of the capacitor 48 is independent of the permittivity and the permeability. The capacitance $\in C_{0co}$ of the capacitor 50 is proportional to the permittivity $\in$ of the sample 4.

Figure 4:
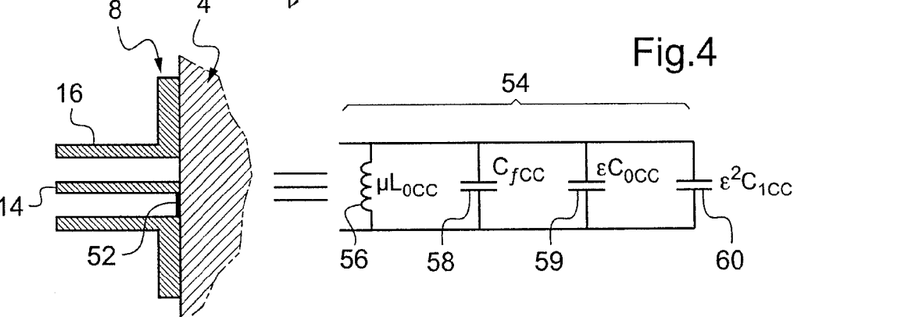

FIG. 4 is a schematic cross-section view of the probe 8 when the switch 34 is in its closed position. The probe 8 is said then to be in a short-circuit. In this figure, the short-circuit between the core 14 and the sheath 16 is represented by a bold line 52.

The probe in short-circuit is modeled by means of a model 54. For example, the model 54 comprises, successively connected in parallel, one inductor 56 and three capacitors 58 to 60. The value $\mu L_{0cc}$ of the inductor 56 is proportional to the permeability $\mu$ of the sample 4. The capacitance $C_{fcc}$ of the capacitor 58 is independent of the permittivity and the permeability. The capacitances $\in C_{0cc}$, and $\in^2 C_{1cc}$ respectively of the capacitors 59 and 60 are a function of the permittivity $\in$ of the sample 4.

From the model 44, it is possible to estimate the admittance $Y_{CO}$ measured by the apparatus 6 in an open circuit. This estimation is given by the following relationship:

$$Y_{CO} = \frac{j\omega(C_{fco} + \varepsilon C_{0co})}{1 - \omega^2(C_{fco} + \varepsilon C_{0co})\mu L_{0co}} \quad (1)$$

where:

$\omega$ is the pulsation ($\omega = 2\pi f$, where f is the working frequency in Hertz), j is the complex number such that $j^2 = -1$, and $L_{0co}$, $C_{fco}$, and $C_{0co}$ are parameters of the model 44 whose values are independent of the permittivity $\in$ and of the permeability $\mu$.

Similarly, from the model 54, it is possible to estimate the admittance $Y_{CC}$ measured by the apparatus 6 in a short-circuit. This estimation is given by the following relationship:

$$Y_{CC} = j\omega(C_{fcc} + \varepsilon C_{0cc} + \varepsilon^2 C_{1cc}) + \frac{1}{j\omega\mu L_{0cc}} \quad (2)$$

where:

$L_{0cc}$, $C_{fcc}$, $C_{0cc}$, and $C_{1cc}$ are parameters of the model 54 whose values are independent of permittivity $\in$ and of the permeability $\mu$.

Figure 5:
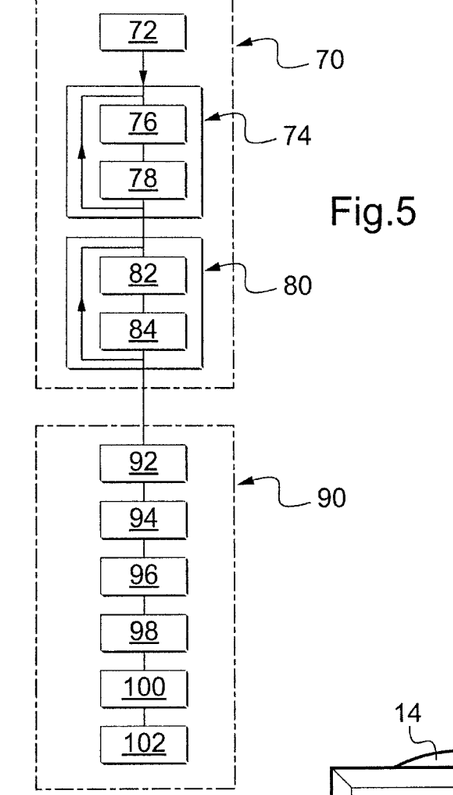
FIG. 5 is a flowchart of a method for measuring the permittivity and the permeability of a sample by means of the device of FIG. 1.

The working of the device 2 shall now be described with reference to the method of FIG. 5.

The method starts with a phase 70 for calibrating the device 2. Initially, at the beginning of this phase 70, at a step 72, the apparatus 6 is calibrated. This step 72 is a conventional step and shall not be described in greater detail.

Then, a step 74 for calibrating the probe 8 in an open circuit is performed. This step 74 is aimed at determining the value of the parameters $C_{fco}$, $C_{0co}$ and $L_{0co}$. For this step 74, the invention uses standard samples. The permittivity and the permeability of these standard samples are known in advance. For example, the step 74 uses three standard samples chosen from the group formed by de-ionized water, Teflon (RM), air and a magnetic-dielectric material whose permittivity and permeability are equal to 5.

More specifically, in an operation 76, the first standard sample is placed instead of the sample 4. In other words, the probe 8 is applied to a plane face of this standard sample. Then, under these conditions, the admittance $Y_{ref1co}$ is measured by the apparatus 6. Then, the operation 76 is repeated for the second and third standard samples so as to measure the admittance values $Y_{ref2co}$ and $Y_{ref3co}$ respectively.

Then, in an operation 78, the computer 20 determines the values of the parameters $C_{0co}$, $C_{fco}$ and $L_{0co}$ from the measurements $Y_{ref1co}$, $Y_{ref2co}$ and $Y_{ref3co}$ as well as from the known values of permittivity $\in_{ref1}$, $\in_{ref2}$ and $\in_{ref3}$ and of permeability $\mu_{ref1}$, $\mu_{ref2}$ and $\mu_{ref3}$, respectively of the first, second and third standard samples. For example, to this effect, the following system of equations is resolved:

$$\begin{cases} \dfrac{j\omega(\varepsilon_{ref1}C_{0co} + C_{fco})}{-\omega^2(C_{fco} + \varepsilon_{ref1}C_{0co})\mu_{ref1}L_{0co} + 1} = Y_{ref1co} \\ \dfrac{j\omega(\varepsilon_{ref2}C_{0co} + C_{fco})}{-\omega^2(C_{fco} + \varepsilon_{ref2}C_{0co})\mu_{ref2}L_{0co} + 1} = Y_{ref2co} \\ \dfrac{j\omega(\varepsilon_{ref3}C_{0co} + C_{fco})}{-\omega^2(C_{fco} + \varepsilon_{ref3}C_{0co})\mu_{ref3}L_{0co} + 1} = Y_{ref3co} \end{cases} \quad (3)$$

The value of the parameters $C_{0c0}$, $C_{fco}$ and $L_{0co}$ depends on the working frequency of the electromagnetic wave and therefore on the frequency of the excitation current flowing in the core 16 used to measure the admittance. Consequently, the operations 76 and 78 are preferably repeated for a large number of different frequencies evenly distributed in the range of possible working frequencies. For example, this range of possible working frequencies extends from 0 MHz to 20 GHz. Preferably, the range of working frequencies is from 100 MHz to 10 GHz.

Once the step 74 is completed, a step 80 is performed for calibrating the probe 8 in short-circuit. To this end, the switch 34 is switched over into its closed position and the admittance of four standard samples is measured by means of the device 2 in an operation 82. As above, the known values of permittivity and permeability of these standard samples are denoted respectively as $\in_{ref1}$, $\in_{ref2}$, $\in_{ref3}$ and $\in_{ref4}$ while the known values of permeability are denoted as $\mu_{ref1}$, $\mu_{ref2}$, $\mu_{ref3}$ and $\mu_{ref4}$. The standard samples are for example chosen out of the same group as the one described with reference to the step 74.

In an operation 82, the respective admittance values $Y_{ref1}$, $Y_{ref2}$, $Y_{ref3}$ and $Y_{ref4}$ of each of these standard samples are measured by means of the apparatus 6.

Then, in an operation 84, the values of the parameters $C_{fcc}$, $C_{0cc}$, $C_{1cc}$ and $L_{0cc}$ are computed from the measured admittance values $Y_{ref1}$, $Y_{ref2}$, $Y_{ref3}$ and $Y_{ref4}$ as well as from the known values of permeability and permittivity of the standard samples. For example, at the operation 84, the following system of equations is resolved:

$$\begin{cases} Y_{ref1} = j\omega(C_{fcc} + \varepsilon_{ref1}C_{0cc} + \varepsilon_{ref1}^2 C_{1cc}) + \dfrac{1}{j\omega\mu_{ref1}L_{0cc}} \\ Y_{ref2} = j\omega(C_{fcc} + \varepsilon_{ref2}C_{0cc} + \varepsilon_{ref2}^2 C_{1cc}) + \dfrac{1}{j\omega\mu_{ref2}L_{0cc}} \\ Y_{ref3} = j\omega(C_{fcc} + \varepsilon_{ref3}C_{0cc} + \varepsilon_{ref3}^2 C_{1cc}) + \dfrac{1}{j\omega\mu_{ref3}L_{0cc}} \\ Y_{ref4} = j\omega(C_{fcc} + \varepsilon_{ref4}C_{0cc} + \varepsilon_{ref4}^2 C_{1cc}) + \dfrac{1}{j\omega\mu_{ref4}L_{0cc}} \end{cases} \quad (4)$$

The operations 82 and 84 are reiterated for several working frequencies evenly distributed in the range of working frequencies. Preferably, the same working frequencies as those used in the step 74 are used in the step 80.

Once the device 2 has been calibrated, the phase 70 is terminated and a phase 90 for measuring permittivity and permeability of the sample 4 can be activated.

At the start of the phase 90, in a step 92, the probe 8 is placed so as to lean on the face 12 of the sample 4 for which the permittivity $\in_{test}$ and the permeability $\mu_{test}$ have to be measured.

Then, at a step 94, the switch 30 is switched over to its open position and the admittance $Y_{testco}$ is measured by means of the apparatus 6. Preferably, the step 94 is reiterated for the same working frequencies as those used in the step 74 so that several measurements of admittance $Y_{testco}$ are obtained.

Then, at a step 96, the switch is switched over to its closed position.

Then, at a step 98, the admittance $Y_{testcc}$ is measured by the apparatus 6 for the different working frequencies used.

At a step 100, the computer 20 computes the permittivity $\in_{test}$ and the permeability $\mu_{test}$ for each of the working frequencies used during the steps 94 and 98. The permeability $\in_{test}$ and the permeability $\mu_{test}$ are each obtained from the admittance values $Y_{testco}$ and $Y_{testcc}$ measured at the same frequency. For example, the permittivity $\in_{test}$ and the permeability $\mu_{test}$ are computed by resolving the following system of equations:

$$\begin{cases} y_{testco} - \dfrac{j\omega(C_{fco} + \varepsilon_{test}C_{0co})}{1 - \omega^2(C_{fco} + \varepsilon_{test}C_{0co})\mu_{test}L_{0co}} = 0 \\ y_{testcc} - j\omega(C_{fcc} + \varepsilon_{test}C_{0cc} + \varepsilon_{test}^2 C_{1cc}) - \dfrac{1}{j\omega\mu_{test}L_{0cc}} = 0 \end{cases} \quad (5)$$

where:

$C_{fco}$, $C_{0co}$, $L_{0co}$, $L_{0cc}$, $C_{fcc}$, $C_{0cc}$ and $C_{1cc}$ are the values of the parameters measured or interpolated on the basis of the measurements made during the phase 70, $Y_{testco}$ and $Y_{testcc}$ test are the admittance values measured in open circuit and in closed circuit for this working frequency.

The above system of equations can be resolved analytically. However, it has three solutions. To choose the right solution, the solution having the permittivity closest to 1 is chosen. For example, to this end, this system of equations is resolved by means of a Newton-type resolution initialized by taking the permittivity value $\mu_{test}$ equal to 1.

Once the permittivity $\in_{test}$ and the permeability $\mu_{test}$ have been computed at the step 100, they are presented during a step 102 to the user through the man-machine interface or recorded in a file.

Figure 6:
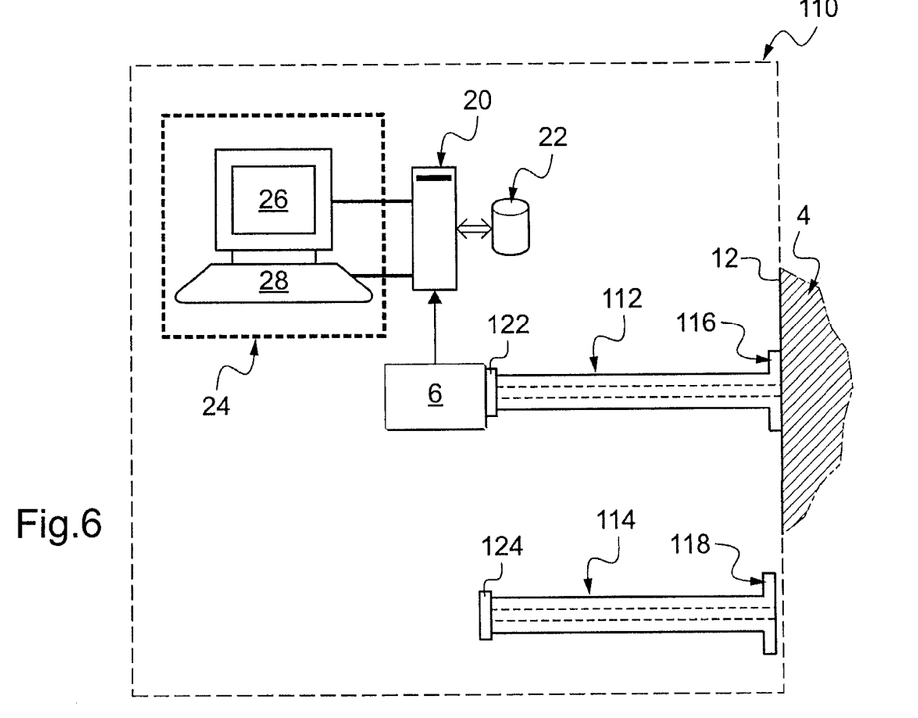
FIG. 6 is a schematic illustration of another embodiment of a device for measuring the permittivity and the permeability of a sample.

FIG. 6 shows another embodiment of a device 110 for measuring the permittivity and the permeability of the sample 4. This device 110 is identical to the device 2 except that the waveguide 10 is replaced by two waveguides 112 and 114. The waveguides 112 and 114 respectively have ends 116 and 118 that are to lean directly on the face 12 when a measurement of admittance is made. The end 116 forms an open-circuit probe. For example, the end 116 is identical to the probe 8 except that the switch 34, the conductors 36 and 38 and the control unit 36 have been omitted. Thus, the probe 116 has only an open-circuit configuration.

Figure 7:
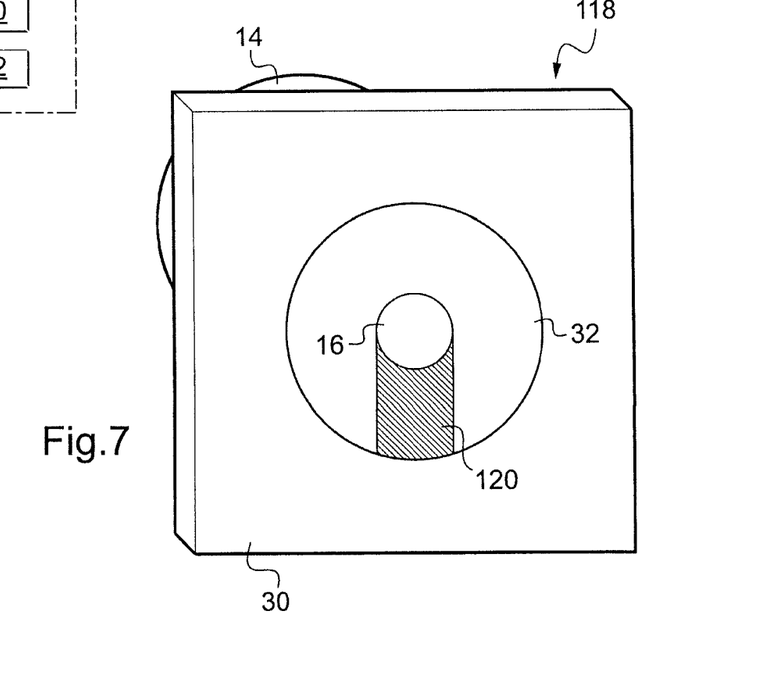
FIG. 7 is a schematic illustration in perspective of one end of a waveguide of the measuring device of FIG. 6.

Conversely, the end 118 forms a probe having only a partial short-circuit configuration. This probe 118 is shown in greater detail in FIG. 7. This probe 118 is for example identical to the probe 8 except that the switch 34 and the conductors 36 and 38 are replaced by a thin metal plate 120 which extends from the core 16 to the sheath 14. The dimensions of this plate 120 are sufficient to modify the phase and/or the amplitude of the electromagnetic waves reflected by the face 12 as compared with the case where the plate is omitted. For example, this modification of the phase and/or of the amplitude is at least greater than 1% or 10% of the phase and/or of the amplitude obtained when the plate 120 is omitted. For example, the width of the plate 120 is equal to the diameter of the core 16.

The other end of each of the waveguides 112 and 114 is equipped respectively with connectors 122 and 124. These connectors 122 and 124 enable the connection and, alternately, the disconnection of the waveguides 112 and 114 to/from the apparatus 6.

The working of the device 110 is identical to the one described with reference to the method of FIG. 5 except that to pass from the probe in open circuit to the probe in closed circuit, it is necessary here to replace the waveguide 112 by the waveguide 114 and vice versa.

Many other embodiments are possible. For example, the section of the waveguides is not necessarily circular as in the case of coaxial cables. For example, the sections of the sheath and/or of the core may be rectangular.

The waveguide may have several cores.

In the device 110, the condition by which the first and second waveguides are structurally identical with the exception of the metal plate 120 is not necessary. For example, the dimensions of the waveguides 112 and 114 may differ. For example, the dimensions of the sheath and of the core (for example their respective diameters) may be different between these two waveguides.

As a variant, the computer computes only the permittivity from the measured admittance values $Y_{testco}$ and $Y_{testcc}$ without delivering the value of the permeability $\mu_{test}$ to the user. This makes it possible to measure the permittivity of material for which the permeability is different from 1 (for example ferrite). Conversely, the computer can also compute only the permeability $\mu_{test}$ from the admittance values measured $Y_{testco}$ and $Y_{testcc}$ without delivering the permittivity value $\in_{test}$ to the user.

Electrical models other than those represented here can be used provided that they show the permittivity and the permeability of the sample. These other models may be obtained from equations of the radiation of the electromagnetic waves. In particular, more complex models may be used instead of those shown.

The end of each waveguide does not necessarily take the form of a probe. For example, the end of the waveguide may be directly applied to the sample without having any clamp or similar means.

Here, the devices 2 and 110 have been described in the particular case where the measurements of admittance are directly transmitted to the computer by means of a wire link. As a variant, this wire link is omitted and the measurements made by the apparatus 6 are entered through the keyboard 28 in order to communicate them to the computer 20 which is responsible for making computations of permittivity and permeability.

Finally, the devices 2 and 110 and the different systems of equations have been described in the particular case where the variables measured are admittance values. However, the devices 2 and 110 can be adapted to measuring not admittance values directly but a variable representing admittance. The term "variable representing an admittance" designates a physical variable that can be measured by means of an apparatus and from which it is possible to deduce the value of the admittance without any complementary measurements. For example the impedance and the coefficient of reflection of the electromagnetic waves on the face 12 are variables representing admittance. Should a variable representing admittance other than admittance itself be used, then the systems of equations described here above are adapted in order to take account of this difference.

The invention claimed is:

1. A method for measuring the permittivity and/or the permeability of a sample of non-conductive material, said method comprising:

measuring a variable representing an admittance $Y_{testco}$ solely from amplitude and phase of electromagnetic waves reflected from an interface between the sample and one end of a first waveguide, said one end of said first waveguide having
at least one conductive core separated from a conductive sheath by a layer made of dielectric material through which the electromagnetic waves are propagated;

measuring a variable representing an admittance $Y_{testcc}$ solely from the amplitude and the phase of the electromagnetic waves reflected from the interface between the sample and an end of a second waveguide, said second waveguide having
at least one conductive core separated from a conductive sheath by a layer of dielectric material through which the electromagnetic waves are propagated, and
a short-circuit between said core and said sheath made at the interface with the sample so that the phase and/or the amplitude of the electromagnetic waves reflected from the sample are different from those obtained in the absence of a short-circuit, and at least one of
computing a permittivity of the sample from the variables representing values of admittance $Y_{testco}$ and $Y_{testcc}$, and computing a permeability of the sample from the variables representing the values of admittance $Y_{testco}$ and $Y_{testcc}$.

2. The method of claim 1, wherein, between measuring a variable representing an admittance $Y_{testco}$ and measuring a variable representing an admittance $Y_{testcc}$, said method further comprises:

switching over of a switch electrically connected between the core and the sheath to pass from the first waveguide where the core and the sheath are electrically insulated from each other to the second waveguide where the core and the sheath are electrically short-circuited.

3. The method of claim 1, wherein the measurements of the variables representing values $Y_{testco}$ and $Y_{testcc}$ are made with electromagnetic waves of a same frequency.

4. A non-transitory and tangible information-recording medium having, encoded thereon in a tangible and non-transitory form, software for measuring permittivity and permeability of a sample of non-conductive material, said software comprising instructions for causing:

measurement of a variable representing an admittance $Y_{testco}$ solely from amplitude and phase of electromagnetic waves reflected from an interface between the sample and one end of a first waveguide, said one end of said first waveguide having
at least one conductive core separated from a conductive sheath by a layer made of dielectric material through which the electromagnetic waves are propagated;

measurement of a variable representing an admittance $Y_{testcc}$ solely from the amplitude and the phase of the electromagnetic waves reflected from the interface between the sample and an end of a second waveguide, said second waveguide having
at least one conductive core separated from a conductive sheath by a layer of dielectric material through which the electromagnetic waves are propagated, and
a short-circuit between said core and said sheath made at the interface with the sample so that the phase and/or the amplitude of the electromagnetic waves reflected from the sample are different from those obtained in the absence of a short-circuit, and
at least one of
computation of a permittivity of the sample from the variables representing values of admittance $Y_{testco}$ and $Y_{testcc}$, and
computation of permeability of the sample from the variables representing the values of admittance $Y_{testco}$ and $Y_{testcc}$.

5. An apparatus for measuring permittivity and/or permeability of a sample of non-conductive material, said apparatus comprising:

a measurement apparatus for measuring variables representing admittance values solely from amplitude and phase of electromagnetic waves reflected from an interface between the sample and an end of a waveguide, a first waveguide having
a first end configured to be applied to the sample, and a second opposite end configured to be connected to the measuring apparatus to measure a variable representing an admittance $Y_{testco}$, the first waveguide being equipped with at least one conductive core separated from a conductive sheath by a layer made of dielectric material through which the electromagnetic waves are propagated, a second waveguide having a first end configured to be applied to the sample, and a second opposite end configured to be connected to the measuring apparatus to measure a variable representing an admittance $Y_{testcc}$,
said second waveguide being equipped with at least one conductive core separated from a conductive sheath by a layer of dielectric material through which the electromagnetic waves are propagated, and having a short-circuit between the core and the sheath made at the interface with the sample so that the phase and/or the amplitude of the electromagnetic waves reflected from the sample are different from those obtained in the absence of a short-circuit, and a computer configured to perform at least one of computing permittivity of the sample from the variables representing values of admittance $Y_{testco}$ and $Y_{testcc}$, and computing permeability of the sample from the variables representing the values of admittance $Y_{testco}$ and $Y_{testcc}$.

6. The apparatus of claim 5, wherein:
the first and second waveguides are structurally identical, and wherein the device further comprises a switch electrically connected between the core and the sheath to pass from the first waveguide, where the core and the sheath are electrically insulated from one another, to the second waveguide, where the core and the sheath are short-circuited.

7. The apparatus of claim 5, wherein the first end of the second waveguide comprises a metal plate extending from the core to the sheath to short-circuit the core and the sheath and obstruct only one part of the section of the dielectric material through which the electromagnetic waves reflected from the sample are propagated.

8. The apparatus of claim 7, wherein the second waveguide is identical to the first waveguide except that the second waveguide comprises said metal plate.

9. The apparatus of claim 5, wherein the sheath completely surrounds the core.

* * * * *